US005599539A

United States Patent [19]
Carroll et al.

[11] Patent Number: 5,599,539
[45] Date of Patent: Feb. 4, 1997

[54] THERAPY FOR CLOSTRIDIAL BOTULINUM TOXIN

[75] Inventors: Sean B. Carroll; Margaret B. van Boldrik, both of Cottage Grove; Christopher M. Clemens, Madison, all of Wis.

[73] Assignee: Ophidian Pharmaceuticals, Inc., Madison, Wis.

[21] Appl. No.: 255,009

[22] Filed: Jun. 7, 1994

Related U.S. Application Data

[63] Continuation of Ser. No. 985,321, Dec. 4, 1992, which is a continuation-in-part of Ser. No. 842,709, Feb. 26, 1992, which is a continuation-in-part of Ser. No. 429,791, Oct. 31, 1989, Pat. No. 5,196,193.

[51] Int. Cl.$^6$ ........................ A61K 31/395; C07K 16/02; C07K 16/12
[52] U.S. Cl. ..................................... 424/167.1; 424/164.1; 424/157.1; 530/389.1; 530/389.5; 530/853
[58] Field of Search .............................. 424/157.1, 164.1, 424/167.1; 530/389.1, 389.5, 853

[56] References Cited

U.S. PATENT DOCUMENTS

5,196,193  3/1993  Carroll .................................. 424/157.1

OTHER PUBLICATIONS

C. L. Hatheway, "Toxigenic Clostridia," Clin. Microbiol. Rev., 3:66 (1990).
S. Arnon, "Infant Botulism: Anticipating the Second Decade," J. Infect. Dis., 154:201 (1986).
S. Arnon, "Infant Botulism," Ann. Rev. Med., 31:541, (1980).
K. L. MacDonald et al., "The Changing Epidemiology of Adult Botulism in the United States," Am. J. Epidemiol., 124:794 (1986).
C. O. Tacket et al., "Equine Antitoxin Use and Other Factors That Predict Outcome in Type A Foodborne Botulism," Am. J. Med., 76:794 (1984).
M. N. Swartz, "Anaerobic Spore–forming Bacilli: The Clostridia," in *Microbiology*, 4th ed., pp. 633–646 (Davis et al., eds.)(J. B. Lippincott, 1990).
S. Arnon et al., "Infant Botulism: Epidemiology and Relation to Sudden Infant Death Syndrome," Epidemiol. Rev., 3:45 (1981).
Connaught Industries Inc., "Botulism Antitoxin Trivalent (Equine)," Package insert.
T. L. Frankovich et al., "Clinical Trial of Botulism Immune Globulin For Infant Botulism," West. J. Med., 54:103 (1991).
M. Balady, "Botulism Antitoxin Fielded For Operation Desert Storm," USAMRDC Newsletter, p. 6 (1991).
P. J. Schwarz et al., "Botulism Immune Globulin For Infant Botulism Arrives—One Year and A Gulf War Later," West. J. Med., 156:197 (1992).
D. R. Peterson et al., "The Sudden Infant Death Syndrome and Infant Botulism," Rev. Infect. Dis., 1:630 (1979).
S. Arnon et al., "Intestinal Infection and Toxin Production by *Clostridium botulinum* As One Cause of Sudden Infant Death Syndrome," Lancet p. 1273 (17 Jun. 1978).
H. N. Benson et al., "Requirement of Avian C'1 For Fixation of Guinea Pig Complement by Avian Antibody–antigen Complexes," J. Immunol., 87:616 (1961).
Benedict et al., "Immunoglobulins and Antibody Production in Avian Species," in *Comparative Immunology*, pp. 335–375, (J. J. Marchaloni, ed.)(Blackwell, Oxford, 1966).
Patterson et al., "Antibody Production and Transfer to Egg Yolk in Chickens," J. Immunol., 898:272 (1962).
Carroll et al., "Antibodies to Calf Thymus RNA Polymerase II From Egg Yolks of Immunized Hens," J. Biol. Chem., 258:24 (1983).
Polson et al., "Antibodies to Proteins From Yolk of Immunized Hens," Immunol. Comm., 9:495 (1980).
Delmee et al., "Characterization of Flagella of *Clostridium difficile* and Their Role in Serogrouping Reactions," J. Clin. Microbiol., 28:2210 (1990).
Delmee et al., "Virulence of Ten Serogroups of *Clostridium difficile* in Hamsters," J. Med. Microbiol., 33:85 (1990).
Toma et al., "Serotyping of *Clostridium difficle*," J. Clin. Microbiol., 26:426 (1988).
Delmee et al., "Serogrouping of *Clostridium difficile* strains by slide agglutination," J. Clin. Microbiol., 21:323 (1985).
Davies et al., "Detection of Capsule in Strains of *Clostridium difficile* of Varying Virulence and Toxigenicity," Microbiol. Path., 9:141 (1990).
S. M. Finegold et al., *Bailey and Scott's Diagnostic Microbiology*, pp. 488–489 (C. V. Mosby Co., 1978).
N. V. Padhye et al., "Production and Characterization of a Monoclonal Antibody Specific For Enterohemorrhagic *Escherichia coli* of Serotypes 0157:H7 and 026:H11," Clin. Microbiol., 29:99 (1990).
D. M. Lyerly et al., "Passive Immunization of Hamsters Against Disease Caused by *Clostridium difficle* by Use of Bovine Immunoglobulin G Concentrate," Infect. Immun., 59:2215 (1991).
B. R. DasGupta et al., "Purification and Amino Acid Composition of Type A Botulinum Neurotoxin," Toxicon, 22:415 (1984).
B. R. Singh et al., "Molecular Differences Between Type A Botulinum Neurotoxin and its Toxoid," Toxicon, 27:403 (1989).
H. Towbin et al., "Electrophoretic Transfer of Proteins From Polyacrylamide Gels to Nitrocellulose Sheets: Procedure and Some Applications,"Proc. Natl. Acad. Sci, USA, 76:4350 (1979).

(List continued on next page.)

Primary Examiner—Frank C. Eisenschenk
Attorney, Agent, or Firm—Medlen & Carroll, LLP

[57] ABSTRACT

Treating humans and animals intoxicated with a bacterial toxin by administration of antitoxin. Avian antitoxin in an aqueous solution in therapeutic amount that is orally administrable.

10 Claims, 2 Drawing Sheets

OTHER PUBLICATIONS

K. Weber et al., "Proteins and Sodium Dodecyl Sulfate: Molecular Weight Determination on Polyacrylamide Gels and Related Procedures," in *The Proteins*, 3d Edition (H. Neurath & R. L. Hill, eds), pp. 179–223, (Academic Press, NY, 1975).

S. B. Carroll et al., "Production and Purification of Polyclonal Antibodies to the Foreign Segment of β–galactosidase Fusion Proteins," in *DNA Cloning: A Practical Approach*, vol. III, pp. 89–111, (D. Glover, ed), (IRL Press, Oxford, 1987).

B. S. Thalley et al., "Rattlesnake and Scorpion Antivenoms From the Egg Yolks of Immunized Hens," Bio/Technol. 8:934 (1990).

I. Ohishi et al., "Oral Toxicities of *Clostridium botulinum* Toxins in Response to Molecular Size," Infect. Immun., 16:107 (1977).

B. W. Wren et al., "Antigenic Cross–Reactivity and Functional Inhibition by Antibodies to *Clostridium difficle* Toxin A, *Streptococcus mutans* Glucan–Binding Protein, and a Synthetic Peptide," Infect. Immun., 59:3151 (1991).

R. W. Byard, "Possible Mechanisms Responsible For the Sudden Infant Death Syndrome," J. Paediatr. Child Health 27:147 (1991).

M. S. Schreiner, "Infant Botulism: A Review of 12 Years' Experience at the The Children's Hospital of Philadelphia," Pediatrics 87:159 (1991).

J. Stephen et al., *Bacterial Toxins*, 2d edition, pp. 57–63 (Aspects of Microbiology Series 2, American Society for Microbiology, 1986).

J. K. Chia et al., "Botulism in An Adult Associated With Food–borne Intestinal Infection With *Clostridium botulinum*, " New Eng. J. Med., 315:239 (1986).

Steven S. Arnon, "Infant Botulism," in *Textbook of Pediatric Infectious Diseases*, 3d ed., pp. 1095–1102, (R. D. Feigen and J. C. Cherry, eds.) (W. B. Saunders, Philadelphia, 1992).

Steven S. Arnon, "Clinical Trial of Human Infant Botulism Immune Globulin," in *Botulinum and Tetanus Neurotoxins: Neurotransmission and Biomedical Aspects*, (B. R. DasGupta, ed)(Plenum Press, 1992).

Aureli et al., "Two Cases of Type E Infant Botulism Caused by Neurotoxigenic *Clostridium butyricum* in Italy," J. Infect. Dis., 154:207–211 (1986).

E. J. Bowmer, M. C., M.D., "Preparation and Assay of the International Standards for *Clostridium botulinum* types A, B, C, D and E Antitoxins," Bul. Wrld. Hlth. Org., 29:701(1963).

G. M. Thorne et al., "General Characteristics: Nomenclature of Microbial Toxins," in *Pharmacology of Bacterial Toxins, In: International Encyclopedia of Pharmacology and Therapeutics*, pp. 5–16, (Dorner and Drews, Eds.) (Pergamon Press, Oxford) (1986).

M. C. Nahata, "Pediatrics," Chapter 3, *Pharmacotherapy: A Pathophysiologic Approach*, pp. 35–41, (J. T. DePiro et al., eds.) Elsevier, New York, 1989.

D. H. Robinson et al., "Drug Delivery and Administration," Chapter 2, in: *Pharmacotherapy: A Pathophysiologic Approach*, pp. 15–34, (J. T. DePiro et al., eds.) Elsevier, New York, 1989.

E. Abrutyn, "Botulism," Chapter 106, In: *Harrison's Principles of Internal Medicine*, pp. 579–580, (J. D. Wilson et al., eds.), McGraw Hill Inc., New York, 1991.

T. A. Larson, Chapter 81, in: *Pharmacotherapy: A Pathophysiologic Approach*, pp. 1166–1178, (J. T. DiPiro et al., eds.) Elsevier, New York, 1989.

L. S. Siegel, *J. Clin. Microbiol.*, 26 (11): 2351–2356, 1988.

C. Hiraga et al., *Kansesshogaku Zasshi*, 64:118–123. 1990.

Bartz et al., J. Infectious Disease., 1980, 142:439.

Kim et al. Infect. Immun., 1987, 55(12):2984.

Schmidt et al., J. Vet. Med., 36:619, 1989.

FIG. 1

THERAPY FOR CLOSTRIDIAL BOTULINUM TOXIN

This application is a continuation of application Ser. No. 07/985,321, filed Dec. 4, 1992, which is a continuation-in-part of application Ser. No. 07/842,709, filed Feb. 26, 1992, which is a continuation-in-part of application Ser. No. 429,791, filed Oct. 31, 1989 now U.S. Pat. No. 5,196,193.

FIELD OF THE INVENTION

The present invention relates to Clostridial antitoxin therapy for humans and animals.

BACKGROUND OF THE INVENTION

Several species of Clostridia bacteria produce toxins of significance to human and animal health [C. L. Hatheway, Clin. Microbiol. Rev., 3:66–98 (1990)]. The effects of these toxins range from diarrheal diseases that can cause destruction of the colon, to paralytic effects that can cause death. Particularly at risk for developing Clostridial diseases are neonates and humans and animals in poor health (e.g., those suffering from diseases associated with old age or immunodeficiency diseases).

The bacterium *Clostridium botulinum* produces the most poisonous biological toxin known. The lethal human dose is a mere $10^{-9}$ mg/kg bodyweight for toxin in the bloodstream. Botulinal toxin blocks nerve transmission to the muscles, resulting in flaccid paralysis. When the toxin reaches airway and respiratory muscles, it results in respiratory failure that can cause death. [S. Arnon, J. Infectious Diseases, 154:201–206 (1986).]

*C. botulinum* is a spore-forming anaerobe whose habitat is soil and the mud of lakes and ponds. The spores are carried by dust and are found on vegetables taken from the soil, on fresh fruits, and on agricultural products such as honey. Under conditions favorable to the organism, the spores germinate to vegetative cells which produce toxin. [S. Arnon, Ann Rev. Med., 31:541 (1980).]

Botulism disease may be grouped into three types, based on the method of introduction of toxin into the bloodstream. Food-borne botulism results from ingesting improperly preserved and inadequately heated food that contains botulinal toxin. There were 355 cases of food-borne botulism in the United States between 1976 and 1984. [K. L. MacDonald et al., Am. J. Epidemiology, 124:794 (1986).] The death rate due to botulinal toxin is 12% and can be higher in particular risk groups. [C. O. Tacket et al., Am. J. Med., 76:794 (1984).] Wound-induced botulism results from *C. botulinum* penetrating traumatized tissue and producing toxin that is absorbed into the bloodstream. Since 1950, thirty cases of wound botulism have been reported. [M. N. Swartz, *Microbiology*, 4th ed. (1990).] Infectious infant botulism results from *C. botulinum* colonization of the infant intestine with production of toxin and its absorption into the bloodstream. It is likely that the bacterium gains entry when spores are ingested and subsequently germinate. [S. Arnon, J. Infectious Diseases, 154:201–206 (1986).] There have been 500 cases reported since it was first recognized in 1976. [M. N. Swartz, supra.]

Infant botulism strikes infants who are three weeks to eleven months old (greater than 90% of the cases are infants less than six months). [S. Arnon, J. Infectious Diseases, 154:201–206 (1986).] It is believed that infants are susceptible, due, in large part, to the absence of the full adult complement of intestinal microflora. The benign microflora present in the adult intestine provide an acidic environment that is not favorable to colonization by *C. botulinum*. Infants begin life with a sterile intestine which is gradually colonized by microflora. Because of the limited microflora present in early infancy, the intestine is not as acidic, allowing for *C. botulinum* spore germination, growth, and toxin production. In this regard, some adults who have undergone antibiotic therapy which alters intestinal microflora become more susceptible to botulism.

An additional factor accounting for infant susceptibility to infectious botulism is the immaturity of the infant immune system. The mature immune system is sensitized to bacterial antigens and produces protective antibodies. Secretory IgA produced in the adult intestine has the ability to agglutinate vegetative cells of *C. botulinum*. [S. Arnon, J. Infectious Diseases, 154:201–206 (1986).] Secretory IgA may also act by preventing intestinal bacteria and their products from crossing the cells of the intestine. [S. Arnon, Epidemiologic Reviews, 3:45–66 (1981).] The infant immune system is not primed to do this.

Clinical symptoms of infant botulism range from mild paralysis, to moderate and severe paralysis requiring hospitalization, to fulminant paralysis, leading to sudden death. [S. Arnon et al., Epidemiologic Reviews, 3:45–66 (1981).]

The chief therapy for severe infant botulism is ventilatory assistance using a mechanical respirator and concurrent elimination of toxin and bacteria using cathartics, enemas, and gastric lavage. There were 68 hospitalizations in California for infant botulism in a single year with a total cost of over $4 million for treatment. [T. L. Frankovich & S. Arnon, West. J. Med., 154:103 (1991).]

Different types of Clostridium each produce antigenically distinct toxin designated by the letters A–G. Nearly all cases of infant botulism have been caused by bacteria producing either type A or type B toxin. (Exceptionally, one New Mexico case was caused by Clostridium producing type F toxin and another by Clostridium producing a type B-type F hybrid.) [S. Arnon, Epidemiologic Reviews, 3:45–66 (1981).] Type C toxin affects waterfowl, type D toxin affects cattle, and type E toxin affects both humans and birds.

A trivalent antitoxin derived from horse plasma is commercially available from Connaught Industries Ltd. as a therapy for toxin types A, B, and E. However the antitoxin has several disadvantages. First, extremely large dosages must be injected intravenously and/or intramuscularly. Second, the antitoxin has serious side effects such as acute anaphylaxis which can lead to death, and serum sickness. Finally, the efficacy of the antitoxin is uncertain and the treatment is costly. [T. O. Tacket et al., Am. J. Med., 76:794–98 (1984).]

A heptavalent equine botulinal antitoxin which uses only the F(ab')2 portion of the antibody molecule has been tested by the United States Military. [M. Balady, USAMRDC Newsletter, p. 6 (1991).] This was raised against impure toxoids in those large animals and is not a high titer preparation.

A pentavalent human antitoxin has been collected from immunized human subjects for use as a treatment for infant botulism. The supply of this antitoxin is limited and cannot be expected to meet the needs of all individuals stricken with botulism disease. In addition, collection of human sera must involve screening out HIV and other potentially serious human pathogens. [P. J. Schwarz & S. S. Arnon, Western J. Med., 156:197–98 (1992).]

Infant botulism has been implicated as the cause of mortality in some cases of Sudden Infant Death Syndrome (SIDS, also known as crib death). SIDS is officially recognized as infant death that is sudden and unexpected and that remained unexplained despite complete post-mortem examination. The link of SIDS to infant botulism came when fecal or blood specimens taken at autopsy from SIDS infants were found to contain *C. botulinum* organisms and/or toxin in 3–4% of cases analyzed. [D. R. Peterson et al., Reviews of Infect. Dis., 1:630–34 (1979).] In contrast, only 1 of 160 healthy infants (0.6%) had *C. botulinum* organisms in the feces and no botulinal toxin. [S. Arnon et al., *The Lancet*, pp. 1273–77, Jun. 17, 1978.]

In developed countries, SIDS is the number one cause of death in children between one month and one year old. [S. Arnon et al., *The Lancet*, pp. 1273–77, Jun. 17, 1978.] More children die from SIDS in the first year than from any other single cause of death in the first fourteen years of life. In the United States, there are 8,000–10,000 SIDS victims annually. Id.

What is needed is an effective therapy against infant botulism that is free of dangerous side effects, is available in large supply at a reasonable price, and can be safely and gently delivered so that prophylactic application to infants is feasible.

SUMMARY OF THE INVENTION

The present invention contemplates treating humans and animals intoxicated with a bacterial toxin by oral administration of antitoxin raised against the toxin. In one embodiment, the present invention contemplates a method of treatment comprising: a) providing, i) avian antitoxin in an aqueous solution in therapeutic amount that is orally administrable, and ii) at least one intoxicated subject; and b) orally administering the avian antitoxin to subject.

The present invention further contemplates a method of prophylactic treatment comprising: a) providing i) avian antitoxin in an aqueous solution in therapeutic amount that is orally administrable, and ii) at least one infant subject; and b) orally administering the avian antitoxin to subject.

The invention is particularly useful where antitoxin comprises Clostridial antitoxin such as *Clostridial botulinus* antitoxin. In one embodiment, the present invention contemplates that the aqueous solution comprises a nutritional formula, such as infant formula.

As a composition, avian clostridial antitoxin, such as botulinus antitoxin, is contemplated wherein it is in an aqueous solution in therapeutic amounts that is orally administrable. In a preferred embodiment, the aqueous solution is a nutritional formula such as infant formula.

The present invention also contemplates a method of treatment of enteric bacterial infections comprising: a) providing i) avian antitoxin in an aqueous solution in therapeutic amount that is orally administrable, and ii) at least one infected subject; and b) orally administering avian antitoxin to the subject. Such bacterial infections may be infections of *Clostridium botulinus*, *Clostridium butyicum*, *Clostridium difficile*, *Clostridium perfringens*, and *Clostridium sordelli*. The antitoxin may comprise botulinus antitoxin and the aqueous solution may comprises a nutritional formula, such as infant formula.

The present invention also contemplates diagnostic uses for the antitoxins. In one embodiment, the present invention contemplates a method for detecting Clostridial toxin in biological tissues comprising: a) providing, i) a biological tissue, ii) an avian antitoxin raised against the Clostridial toxin, and iii) a reporter antibody substance with binding specificity for the antitoxin; b) adding the antitoxin to biological tissue so that the antitoxin binds to the Clostridial toxin in the biological tissue; c) washing the unbound antitoxin from the biological tissue; d) adding the reporter antibody substance to the biological tissue so that the reporter antibody substance binds to bound antitoxin; e) washing the unbound reporter antibody substance from the biological tissue; and f) detecting the reporter antibody substance bound to the antitoxin bound to the Clostridial toxin so that the Clostridial toxin is detected. In a preferred embodiment, the Clostridial toxin is botulinal toxin.

DESCRIPTION OF THE DRAWINGS

FIG. 1 shows the reactivity of antibotulinum IgY by Western blot.

DESCRIPTION OF THE INVENTION

Figure 2:
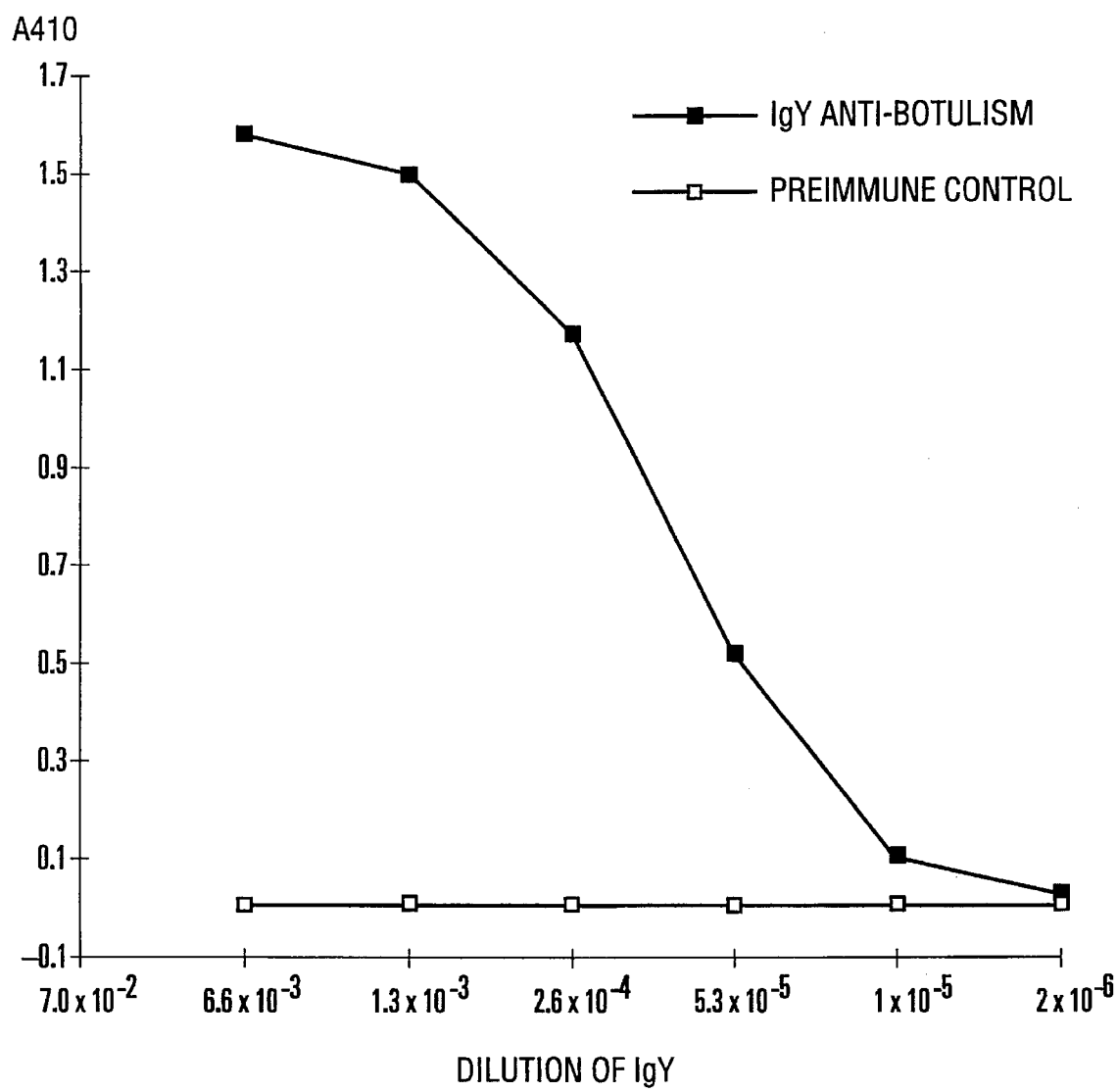
FIG. 2 shows the IgY antibody titer to botulinum type A toxoid of eggs by ELISA.

The present invention contemplates treating humans and animals intoxicated with a bacterial toxin by oral administration of antitoxin raised against the toxin. The individual steps of are described separately below.

I. Obtaining Antibodies in Non-Mammals

A preferred embodiment of the method of the present invention for obtaining antibodies involves immunization. However, it is also contemplated that antibodies could be obtained from non-mammals without immunization. In the case where no immunization is contemplated, the present invention may use non-mammals with preexisting antibodies to toxins as well as non-mammals that have antibodies to whole organisms by virtue of reactions with the administered antigen. An example of the latter involves immunization with synthetic peptides or recombinant proteins sharing epitopes with whole organism components.

In a preferred embodiment, the method of the present invention contemplates immunizing non-mammals with bacterial toxin(s). It is not intended that the present invention be limited to any particular toxin. In one embodiment, toxin from all Clostridial bacteria sources (see Table 1) are contemplated as immunogens. Examples of these toxins are *C. butyicum* neruraminidase toxin, *C. difficile* toxins A and B, *C. perfringens* toxins $\alpha$, $\beta$, E, and $\iota$, and *C. sordelli* toxins HT and LT. In a preferred embodiment, toxins A, B, C, D, E, F, and G from *C. botulinum* are contemplated as immunogens.

TABLE 1

| Clostridial Toxins and Diseases | | |
|---|---|---|
| | TOXINS | DISEASE ASSOCIATION |
| *C. botulinum* | A, B, C, D, E, F, G | Infant botulism, food poisoning |
| *C. butyicum* | neuraminidase | botulism, enterocolitis? |
| *C. difficile* | A, B | pseudomembranous colitis, antibiotic-associated diarrhea, enterocolitis? |
| *C. perfringens* | alpha, beta, epsilon, iota-toxins | gas gangrene, food poisoning |
| *C. sordelli* | HT, LT | diarrhea, gas gangrene |

When immunization is used, the preferred non-mammal is from the class Aves. All birds are contemplated (e.g., duck, ostrich, emu, turkey, etc.). A preferred bird is a chicken.

Importantly, chicken antibody does not fix mammalian complement. (See H. N. Benson et al., J. Immunol., 87:610 (1961).) Thus, chicken antibody will normally not cause a complement-dependent reaction. [A. A. Benedict and K. Yamaga, *Comparative Immunology*, (J. J. Marchaloni, ed.), Ch. 13, "Immunoglobulins and Antibody Production in Avian Species," pp. 335–375, Blackwell, Oxford (1966).] Thus, the preferred antitoxins of the present invention will not exhibit complement-related side effects observed with antitoxins known presently.

When birds are used, it is contemplated that the antibody will be obtained from either the bird serum or the egg. A preferred embodiment involves collection of the antibody from the egg. Laying hens export immunoglobulin to the egg yolk ("IgY") in concentrations equal to or exceeding that found in serum. (See R. Patterson et al., J. Immunol., 89:272 (1962).) [S. B. Carroll and B. D. Stollar, J. Biol. Chem., 258:24 (1983).] In addition, the large volume of egg yolk produced vastly exceeds the volume of serum that can be safely obtained from the bird over any given time period. Finally, the antibody from eggs is purer and more homogeneous; there is far less non-immunoglobulin protein (as compared to serum) and only one class of immunoglobulin is transported to the yolk.

When considering immunization with toxins, one may consider modification of the toxins to reduce its toxicity. In this regard, it is not intended that the present invention be limited by immunization with modified toxin. Unmodified ("native") toxin is also contemplated as an immunogen.

It is also not intended that the present invention be limited by the type of modification—if modification is used. The present invention contemplates all types of toxin modification, including chemical and heat treatment of the toxin. The preferred modification, however, is formaldehyde treatment.

It is not intended that the present invention be limited to a particular mode of immunization; the present invention contemplates all modes of immunization, including subcutaneous, intramuscular, intraperitoneal, and intravascular injection.

The present invention further contemplates immunization with or without adjuvant. (Adjuvant is defined as a substance known to increase the immune response to other antigens when administered with other antigens.) If adjuvant is used, it is not intended that the present invention be limited to any particular type of adjuvant—or that the same adjuvant, once used, be used all the time. While the present invention contemplates all types of adjuvant, whether used separately or in combinations, the preferred use of adjuvant is the use of Complete Freund's Adjuvant followed sometime later with Incomplete Freund's Adjuvant.

When immunization is used, the present invention contemplates a wide variety of immunization schedules. In one embodiment, a chicken is administered toxin(s) on day zero and subsequently receives toxin(s) in intervals thereafter. It is not intended that the present invention be limited by the particular intervals or doses. Similarly, it is not intended that the present invention be limited to any particular schedule for collecting antibody. The preferred collection time is sometime after day 100.

Where birds are used and collection of antibody is performed by collecting eggs, the eggs may be stored prior to processing for antibody. It is preferred that storage of the eggs be performed at 4° C. for less than one year.

It is contemplated that chicken antibody produced in this manner can be buffer-extracted and used analytically. While unpurified, this preparation can serve as a reference for activity of the antibody prior to further manipulations (e.g., immunoaffinity purification).

II. Increasing the Effectiveness of Antibodies

When purification is used, the present invention contemplates purifying to increase the effectiveness of both non-mammalian antitoxins and mammalian antitoxins. Specifically, the present invention contemplates increasing the percent of toxin-reactive immunoglobulin. The preferred purification approach for avian antibody is Polyethylene Glycol (PEG) separation.

A. PEG Purification

The present invention contemplates that avian antibody be initially purified using simple, inexpensive procedures. In one embodiment, chicken antibody from eggs is purified by extraction and precipitation with polyethylene glycol (PEG). PEG purification exploits the differential solubility of lipids (which are abundant in egg yolks) and yolk proteins in high concentrations of polyethylene glycol 8000. [Polson et al., Immunol. Comm., 9:495 (1980).] The technique is rapid, simple, and relatively inexpensive and yields an immunoglobulin fraction that is significantly purer in terms of contaminating non-immunoglobulin proteins than the comparable ammonium sulfate fractions of mammalian sera and horse antibodies. Indeed, PEG-purified antibody is sufficiently pure that the present invention contemplates the use of PEG-purified antitoxins in the passive immunization of intoxicated humans and animals.

III. Treatment

The present invention contemplates antitoxin therapy for humans and animals intoxicated by bacterial toxins. A preferred method of treatment is by oral administration of antitoxin.

A. Dosage of Antitoxin

It was noted by way of background that a balance must be struck when administering currently available antitoxin; sufficient antitoxin must be administered to neutralize the toxin, but not so much antitoxin as to increase the risk of untoward side effects. These side effects are caused by i) patient sensitivity to horse proteins, ii) anaphylactic or immunogenic properties of non-immunoglobulin proteins, iii) the complement fixing properties of mammalian antibodies, and/or iv) the overall burden of foreign protein administered. It is extremely difficult to strike this balance when, as noted above, the degree of intoxication (and hence the level of antitoxin therapy needed) can only be approximated.

The present invention contemplates significantly reducing side effects so that this balance is more easily achieved. Treatment according to the present invention contemplates reducing side effects by using PEG-purified antitoxin from birds.

In one embodiment, the treatment of the present invention contemplates the use of PEG-purified antitoxin from birds. The use of yolk-derived, PEG-purified antibody as antitoxin allows for the administration of 1) non(mammalian)-complement-fixing, avian antibody, 2) a less heterogeneous mixture of non-immunoglobulin proteins, and 3) less total protein to deliver the equivalent weight of active antibody present in currently available antitoxins. The non-mammalian source of the antitoxin makes it useful for treating patients who are sensitive to horse or other mammalian serums.

B. Delivery of Antitoxin

The present invention contemplates a method for antitoxin treatment of bacterial intoxication in which delivery of antitoxin in an aqueous solution. The solution has sufficient ionic strength to solubilize antibody protein yet is made palatable for oral administration. In one embodiment the delivery solution is an aqueous solution. In another embodiment the delivery solution is a nutritional formula. Preferably, the delivery solution is infant formula.

The invention contemplates a method of treatment which can be administered for treatment of acute intoxication. In one embodiment, antitoxin is administered orally, in a delivery solution, in therapeutic dosage, to a subject intoxicated by the bacterial toxin which served as immunogen for the antitoxin.

The invention also contemplates a method of treatment which can be administered prophylactically. In one embodiment, antitoxin is administered orally, in a delivery solution, in therapeutic dosage, to a subject, to prevent intoxication of the subject by the bacterial toxin which served as immunogen for the antitoxin. In a preferred embodiment the subject is an infant. In another embodiment, antibody raised against whole bacterial organism is administered orally to a subject, in a delivery solution, in therapeutic dosage.

IV. Detection of Toxin

The invention contemplates detecting bacterial toxin in biological tissues, by a method that utilizes antitoxin raised against the toxin and a reporter substance. The reporter substance comprises an antibody with binding specificity for the antitoxin attached to a molecule which is used to identify the presence of the reporter substance. The biological tissue is first exposed to antitoxin which binds to toxin and is then washed free of substantially all unbound antitoxin. The biological tissue is next exposed to the reporter substance, which binds to antitoxin and is then washed free of substantially all unbound reporter substance. Identification of the reporter substance in the biological tissue indicates the presence of the bacterial toxin.

Experimental

The following examples serve to illustrate certain preferred embodiments and aspects of the present invention and are not to be construed as limiting the scope thereof.

In the disclosure which follows, the following abbreviations apply: °C. (degrees Centigrade); rpm (revolutions per minute); BBS-Tween (borate buffered saline containing Tween); BSA (bovine serum albumin); ELISA (enzyme-linked immunosorbent assay); CFA (complete Freund's adjuvant); IFA (incomplete Freund's adjuvant); IgG (immunoglobulin G); IgY (immunoglobulin Y); $H_2O$ (water); HCl (hydrochloric acid); $LD_{100}$ (lethal dose for 100% of experimental animals); kD (kilodaltons); gm (grams); μg (micrograms); mg (milligrams); ng (nanograms); μl (microliters); ml (milliliters); mm (millimeters); nm (nanometers); μm (micrometer); M (molar); mM (millimolar); $MgCl_2$ (magnesium chloride); NaCl (sodium chloride); $Na_2CO_3$ (sodium carbonate); $OD_{280}$ (optical density of 280 nm); PAGE (polyacrylamide gel electrophoresis); PBS (phosphate buffered saline (150 mM NaCl, 10 mM sodium phosphate buffer, pH 7.2)); PEG (polyethylene glycol); SDS (sodium dodecylsulfate); Tris(tris (hydroxymethyl)aminomethane); w/v (weight to volume); v/v (volume to volume); Amresco (Solon, Ohio); BBL (BBL, Cockeysville, Md.); BioRad (BioRad, Richmond, Calif.); Fisher Biotech (Fisher Biotech, Springfield, N.J.); GIBCO (GIBCO, Grand Island, N.Y.)); Millipore (Millipore Corp., Marlborough, Mass.); (Ross Laboratories, Columbus, Ohio); Sigma (Sigma Chemical Co., St. Louis, Mo.);

EXAMPLE 1

Production of High-Titer Antibodies to *Clostridium difficile* Organisms in a Hen Antibodies to certain pathogenic organisms have been shown to be effective in treating diseases caused by those organisms. It has not been shown whether antibodies can be raised, against the Clostridium pathogen, which would be effective in treating infection by this organism. Accordingly, *C. difficile* was tested as immunogen for production of hen antibodies.

To determine the best course for raising high-titer egg antibodies against whole *C. difficile* organisms, different immunizing strains and different immunizing concentrations were examined. The example involved (a) preparation of the bacterial immunogen, (b) immunization, (c) purification of anti-bacterial chicken antibodies, and (d) detection of anti-bacterial antibodies in the purified IgY preparations.

(a) Preparation of Bacterial Immunogen.

*C. difficile* strains 43594 (serogroup A) and 43596 (serogroup C) were originally obtained from the American Type Culture Collection, Rockville, Md. These two strains were selected because they represent two of the most commonly-occurring serogroups isolated from patients with antibiotic-associated pseudomembranous colitis. [Delmee et al., J. Clin. Microbiol., 28(10):2210 (1990).] Additionally, both of these strains have been previously characterized with respect to their virulence in the Syrian Hamster Model for *C. difficile* infection. [Delmee et al., J. Med Microbiol., 33:85 (1990).]

The bacterial strains were separately cultured on brain heart infusion agar for 48 hours at 37° C. in a Gas Pack 100 Jar (BBL, Cockeysville, Md.) equipped with a Gas Pack Plus anaerobic envelope (BBL). Forty-eight hour cultures were used because they produce better growth and the organisms have been found to be more cross-reactive with respect to their surface antigen presentation. The greater the degree of cross-reactivity of our IgY preparations, the better the probability of a broad range of activity against different strains/serogroups. [Toma et al., J. Clin. Microbiol., 26(3):426 (1988).]

The resulting organisms were removed from the agar surface using a sterile dacron-tip swab, and were suspended in a solution containing 0.44 formaldehyde in PBS, pH 7.2. This concentration of formaldehyde has been reported as producing good results for the purpose of preparing whole-organism immunogen suspensions for the generation of polyclonal anti-*C. difficile* antisera in rabbits. [Delmee et al., J. Clin. Microbiol., 21(3):323 (1985); Davies et al., Microbial Path., 9:141 (1990).] In this manner, two separate bacterial suspensions were prepared, one for each strain. The two suspensions were then incubated at 4° C. for 1 hour Following this period of formalin-treatment, the suspensions were centrifuged at 4,200×g for 20 min., and the resulting pellets were washed twice in normal saline. The washed pellets, which contained formalin-treated whole organisms, were resuspended in fresh normal saline such that the visual turbidity of each suspension corresponded to a #7 McFarland standard. [S. M. Finegold et al., Bailey and Scott's Diagnostic Microbiology, pp. 488–489, The C. V. Mosby Co., (1978).] Each of the two #7 suspensions was then split into two separate volumes. One volume of each suspension was volumetrically adjusted, by the addition of saline, to correspond to the visual turbidity of a #1 McFarland standard. [S. M. Finegold et al., *Bailey and Scott's Diagnostic Microbiology*, pp. 488–489, The C. V. Mosby Co., (1978).] The #1 suspensions contained approximately $3\times10^8$ organisms/ml, and the #7 suspensions contained approximately $2\times10^9$ organisms/ml. [S. M. Finegold et al., *Bailey and Scott's Diagnostic Microbiology*, pp. 488–489, The C. V. Mosby Co., (1978).] The four resulting concentration-adjusted suspensions of formalin-treated *C. difficile* organisms were considered to be "bacterial immunogen suspensions." These suspensions were used immediately after preparation for the initial immunization (see section (b)).

The formalin-treatment procedure did not result in 100% non-viable bacteria in the immunogen suspensions. In order to increase this, the formalin concentration and length of treatment were both increased for subsequent immunogen preparations, as described below in Table 3. (Although viability was decreased with the stronger formalin treatment, 100% inviability of the bacterial immunogen suspensions was not reached.) Also, in subsequent immunogen preparations, the formalin solutions were prepared in normal saline instead of PBS. At day 49, the day of the fifth immunization, the excess volumes of the four previous bacterial immunogen suspensions were stored frozen at −70° C. for use during all subsequent immunizations.

(b) Immunization.

For the initial immunization, 1.0 ml volumes of each of the four bacterial immunogen suspensions described above were separately emulsified in 1.2 ml volumes of CFA (GIBCO, Grand Island, N.Y.). For each of the four emulsified immunogen suspensions, two four-month old White Leghorn hens (pre-laying) were immunized. (It is not necessary to use pre-laying hens; actively-laying hens can also be utilized.) Each hen received a total volume of approximately 1.0 ml of a single emulsified immunogen suspension via four injections (two subcutaneous and two intramuscular) of approximately 250 µl per site. In this manner, a total of four different immunization combinations, using two hens per combination, were initiated for the purpose of evaluating both the effect of immunizing concentration on egg yolk antibody (IgY) production, and interstrain cross-reactivity of IgY raised against heterologous strains. The four immunization groups are summarized in Table 2.

TABLE 2

Immunization Groups

| GROUP DESIGNATION | IMMUNIZING STRAIN | APPROXIMATE IMMUNIZING DOSE |
|---|---|---|
| CD 43594, #1 | C. diff. 43594 | $1.5 \times 10^8$ org./hen |
| CD 43594, #7 | " | $1.0 \times 10^9$ org./hen |
| CD 43596, #1 | C. diff. 43596 | $1.5 \times 10^8$ org./hen |
| CD 43596, #7 | " | $1.0 \times 10^9$ org./hen |

The time point for the first series of immunizations was designated as "day zero." All subsequent immunizations were performed as described above except that the bacterial immunogen suspensions were emulsified using IFA (GIBCO) instead of CFA, and for the later time point immunization, the stored frozen suspensions were used instead of freshly-prepared suspensions. The immunization schedule used is listed in Table 3.

TABLE 3

Immunization Schedule

| DAY OF IMMUNIZATION | FORMALIN-TREATMENT | IMMUNOGEN PREPARATION USED |
|---|---|---|
| 0 | 1%, 1 hr. | freshly-prepared |
| 14 | 1%, overnight | " |
| 21 | 1%, overnight | " |
| 35 | 1%, 48 hrs. | " |
| 49 | 1%, 72 hrs. | " |
| 70 | " | stored frozen |
| 85 | " | " |
| 105 | " | " |

(c) Purification of Anti-Bacterial Chicken Antibodies.

Groups of four eggs were collected per immunization group between days 80 and 84 post-initial immunization, and chicken immunoglobulin (IgY) was extracted according to a modification of the procedure of A. Polson et al. [Immunol. Comm., 9:495 (1980)]. A gentle stream of distilled water from a squirt bottle was used to separate the yolks from the whites, and the yolks were broken by dropping them through a funnel into a graduated cylinder. The four individual yolks were pooled for each group. The pooled, broken yolks were blended with 4 volumes of egg extraction buffer to improve antibody yield (egg extraction buffer is 0.01M sodium phosphate, 0.1M NaCl, pH 7.5, containing 0.005% Thimerosal), and PEG 8000 (Amresco) was added to a concentration of 3.5%. When all the PEG dissolved, the protein precipitates that formed were pelleted by centrifugation at 13,000×g for 10 minutes. The supernatants were decanted and filtered through cheesecloth to remove the lipid layer, and the PEG was added to the supernatants to a final concentration of 12% (the supernatants were assumed to contain 3.5% PEG). After a second centrifugation, the supernatants were discarded and the pellets were centrifuged a final time to extrude the remaining PEG. These crude IgY pellets were then dissolved in the original yolk volume of egg extraction buffer and stored at 4° C. As an additional control, a preimmune IgY solution was prepared as described above, using eggs collected from unimmunized hens.

(d) Detection of Anti-Bacterial Antibodies in the Purified IgY Preparations.

In order to evaluate the relative levels of specific anti-*C. difficile* activity in the IgY preparations described above, a modified version of the whole-organism ELISA procedure of N. V. Padhye et al. [J. Clin. Microbiol. 29:99–103] was used. Frozen organisms of both *C. difficile* strains described above were thawed and diluted to a concentration of approximately $1 \times 10^7$ org./ml using PBS, pH 7.2. In this way, two separate coating suspensions were prepared, one for each immunizing strain. Into the wells of 96-well microtiter plates (Falcon, Pro-Bind Assay Plates) were placed 100 µl volumes of the coating suspensions. In this manner, each plate well received a total of approximately $1 \times 10^6$ organisms of one strain or the other. The plates were then incubated at 4° C. overnight. The next morning, the coating suspensions were decanted, and all wells were washed three times using PBS. In order to block non-specific binding sites, 100 µl of 0.5% BSA (Sigma, St. Louis, Mo.) in PBS was then added to each well, and the plates were incubated for 2 hours at room temperature. The blocking solution was decanted, and 100 µl volumes of the IgY preparations described above were initially diluted 1:500 with a solution of 0.1% BSA in PBS, and then serially diluted in 1:5 steps. The following dilutions were placed in the wells: 1:500, 1:2,500, 1:62,5000, 1:312,500, and 1:1,562,500. The plates were again incubated for 2 hours at room temperature. Following this incubation, the IgY-containing solutions were decanted, and the wells were washed three times using BBS-tween (0.1M boric acid, 0.025M sodium borate, 1.0M NaCl, 0.1% tween-20), followed by two washes using PBS-tween (0.1% tween-20), and finally, two washes using PBS only. To each well, 100 µl of a 1:750 dilution of rabbit anti-chicken IgG (whole-molecule)-alkaline phosphatase conjugate (Sigma, St. Louis, Mo.) (diluted in 0.1% BSA in PBS) was added. The plates were again incubated for 2 hours at room temperature. The conjugate solutions were decanted and the plates were washed as described above, substituting 50 mM $Na_2Co_3$, pH 9.5 for the PBS in the final wash. The plates were developed by the addition of 100 µl of a solution containing 1 mg/ml para-nitro phenyl phosphate (Sigma, St. Louis, Mo.) dissolved in 50 mM $Na_2CO_3$, 10 mM MgCl$_2$, pH 9.5 to each well, and incubating the plates at room temperature in the dark for 45 minutes. The absorbance of each well was measured at 410 nm using a Dynatech MR 700 plate reader. In this manner, each of the four IgY preparations described above were tested for reactivity against both of the immunizing *C. difficile* strains, and strain-specific, as well as cross-reactive activity was determined.

TABLE 4

Results of the Anti-*C. Difficile* Whole-Organism ELISA

| IgY PREPARATION | DILUTION OF IgY PREP | 43594-COATED WELLS | 43596-COATED WELLS |
|---|---|---|---|
| Cd 43594, #1 | 1:500 | 1.746 | 1.801 |
|  | 1:2,500 | 1.092 | 1.670 |
|  | 1:12,500 | 0.202 | 0.812 |
|  | 1:62,500 | 0.136 | 0.179 |
|  | 1:312,500 | 0.012 | 0.080 |
|  | 1:1,562,500 | 0.002 | 0.020 |
| CD 43594, #7 | 1:500 | 1.780 | 1.771 |
|  | 1:2,500 | 1.025 | 1.078 |
|  | 1:12,500 | 0.188 | 0.382 |
|  | 1:62,500 | 0.052 | 0.132 |
|  | 1:312,500 | 0.022 | 0.043 |
|  | 1:1,562,500 | 0.005 | 0.024 |
| CD 43596, #1 | 1:500 | 1.526 | 1.790 |
|  | 1:2,500 | 0.832 | 1.477 |
|  | 1:12,500 | 0.247 | 0.452 |
|  | 1:62,500 | 0.050 | 0.242 |
|  | 1:312,500 | 0.010 | 0.067 |
|  | 1:1,562,500 | 0 | 0.036 |
| CD 43596, #7 | 1:500 | 1.702 | 1.505 |
|  | 1:2,500 | 0.706 | 0.866 |
|  | 1:12,500 | 0.250 | 0.282 |
|  | 1:62,500 | 0.039 | 0.078 |
|  | 1:312,500 | 0.002 | 0.017 |
|  | 1:1,562,500 | 0 | 0.010 |
| Preimmune IgY | 1:500 | 0.142 | 0.309 |
|  | 1:2,500 | 0.032 | 0.077 |
|  | 1:12,500 | 0.006 | 0.024 |
|  | 1:62,500 | 0.002 | 0.012 |
|  | 1:312,500 | 0.004 | 0.010 |
|  | 1:1,562,500 | 0.002 | 0.014 |

Table 4 shows the results of the whole-organism ELISA. All four IgY preparations demonstrated significant levels of activity, to a dilution of 1:62,500 or greater against both of the immunizing organism strains. Therefore, antibodies raised against one strain were highly cross-reactive with the other strain, and vice versa. The immunizing concentration of organisms did not have a significant effect on organism-specific IgY production, as both concentrations produced approximately equivalent responses. Therefore, the lower immunizing concentration of approximately 1.5×10$^8$ org./hen is the preferred immunizing concentration of the two tested. The preimmune IgY preparation appeared to possess relatively low levels of *C. difficile*-reactive activity to a dilution of 1:500, probably due to prior exposure of the animals to environmental Ciostridia.

An initial whole-organism ELISA was performed using IgY preparations made from single CD 43594, #1 and CD 43596, #1 eggs collected around day 50 (data not shown). Specific titers were found to be 5 to 10-fold lower than those reported in Table 4. These results demonstrate that it is possible to begin immunizing hens prior to the time that they begin to lay eggs, and to obtain high titer specific IgY from the first eggs that are laid. In other words, it is not necessary to wait for the hens to begin laying before the immunization schedule is started.

EXAMPLE 2

Treatment of *C. Difficile* Infection with Anti-*C. Difficile* Antibody

In order to determine whether the immune IgY antibodies raised against whole *C. difficile* organisms were capable of inhibiting the infection of hamsters by *C. difficile*, hamsters infected by these bacteria were utilized [Lyer et al., Infection and Immunity, 59:2215–2218 (1991)]. This example involved: (a) determination of the lethal dose of *C. difficile* organisms; and (b) treatment of infected animals with immune antibody or control antibody in nutritional solution.

(a) Determination of the Lethal Dose of *C. Difficile* Organisms.

Determination of the lethal dose of *C. difficile* organisms was carried out according to the model described by D. M. Lyerly et al. [Infect. and Immun., 59:2215–2218 (1991)]. *C. difficile* strain ATCC 43596 (serogroup C, American Type Culture Collection) was plated on BHI agar and grown anaerobically (BBL Gas Pak 100 system) at 37° C. for 42 hours. Organisms were removed from the agar surface using a sterile dacron-tip swab and suspended in sterile 0.9% NaCl to a density of 10$^8$ organisms/ml.

In order to determine the lethal dose of *C. difficile* in the presence of control antibody and nutritional formula, non-immune eggs were obtained from unimmunized hens and a 12% PEG preparation made as described in Example 1(c). This preparation was redissolved in one fourth the original yolk volume of Ensure, vanilla flavor (Ross Laboratories, Columbus, Ohio).

Starting on day one, groups of female Golden Syrian hamsters (Harland Sprague Dawley, Madison, Wis.), 8–9 weeks old and weighing approximately 100 gm, were orally administered 1 ml of the preimmune/Ensure formula at time zero, 2 hours, 6 hours, and 10 hours At 1 hour, animals were orally administered 3.0 mg Clindamycin HCl (Sigma) in 1 ml of water. This drug predisposes hamsters to *C. difficile* infection by altering the normal intestinal flora. On day two, the animals were given 1 ml of the preimmune IgY/Ensure formula at time zero, 2 hours, 6 hours, and 10 hours. At 1 hour on day two, different groups of animals were inoculated orally with saline (control), or 10$^2$, 10$^4$, 10$^6$, or 10$^8$ *C. difficile* organisms in 1 ml of saline. From days 3–12, animals were given 1 ml of the preimmune IgY/Ensure formula three times daily and observed for the onset of diarrhea and death. Each animal was housed in an individual cage and was offered food and water ad libitum.

Administration of 10$^6$–10$^8$ organisms resulted in death in 3–4 days while the lower doses of 10$^2$–10$^4$ organisms caused death in 5 days. Cecal swabs taken from dead animals indicated the presence of *C. difficile*. Given the effectiveness of the 10$^2$ dose, this number of organisms was chosen for the following experiment to see if hyperimmune anti-*C. difficile* antibody could block infection.

(b) Treatment of Infected Animals with Immune Antibody or Control Antibody in Nutritional Formula.

The experiment in (a) was repeated using three groups of seven hamsters each. Group A received no clindamycin or *C. difficile* and was the survival control. Group B received clindamycin, 10$^2$ *C. difficile* organisms and preimmune IgY on the same schedule as the animals in (a) above. Group C received clindamycin, 10$^2$ *C. difficile* organisms, and hyperimmune anti-*C. difficile* IgY on the same schedule as Group B. The anti-*C. difficile* IgY was prepared as described in Example 1 except that the 12% PEG preparation was dissolved in one fourth the original yolk volume of Ensure (Ross Laboratories, Columbus, Ohio).

All animals were observed for the onset of diarrhea or other disease symptoms and death. Each animal was housed in an individual cage and was offered food and water ad libitum. The results are shown in Table 5.

TABLE 5

The Effect of Oral Feeding of Hyperimmune
IgY Antibody on *C. Difficile* Infection

| ANIMAL GROUP | | TIME TO DIARRHEA[a] | TIME TO DEATH[a] |
|---|---|---|---|
| A | pre-immune IgY only | no diarrhea | no deaths |
| B | Clindamycin, *C. difficile*, preimmune IgY | 30 hrs. | 49 hrs. |
| C | Clindamycin, *C. difficile*, immune IgY | 33 hrs. | 56 hrs. |

[a]mean of seven animals

Hamsters in the control group A did not develop diarrhea and remained healthy during the experimental period. Hamsters in groups B and C developed diarrheal disease. Anti-*C. difficile* IgY did not protect the animals from diarrhea or death, all animals succeed in the same time interval as the animals treated with preimmune IgY. Thus, while immunization with whole organisms apparently can improve sublethal symptoms with particular bacteria (see U.S. Pat. No. 5,080,895 to H. Tokoro), such an approach does not prove to be productive to protect against the lethal effects of *C. difficile*.

EXAMPLE 3

Production of *C. Botulinum* Type A Antitoxin in Hens

In order to determine whether antibodies could be raised against the toxin produced by Clostridial pathogens, which would be effective in treating Clostridial diseases, antitoxin to botulinum type A toxin was produced. This example involves: (a) toxin modification; (b) immunization; (c) antitoxin collection; (d) antigenicity assessment; and (e) assay of antitoxin titer.

(a) Toxin Modification.

Botulinum type A toxoid was obtained from B. R. Das-Gupta. From this, the active type A neurotoxin (M. W. approximately 150 kD) was purified to greater than 99% purity, according to published methods. [B. R. DasGupta & V. Sathyamoorthy, Toxicon, 22:415 (1984).] The neurotoxin was detoxified with formaldehyde according to published methods. [B. R. Singh & B. R. Das Gupta, Toxicon, 27:403 (1989).]

(b) Immunization.

Botulinum toxoid for immunization was dissolved in PBS (1 mg/ml) and was emulsified with an approximately equal volume of CFA (GIBCO) for initial immunization or IFA for booster immunization. On day zero, two white leghorn hens, obtained from local breeders, were each injected at multiple sites (intramuscular and subcutaneous) with 1 ml inactivated toxoid emulsified in 1 ml CFA. Subsequent booster immunizations were made according to the following schedule for day of injection and toxoid amount: days 14 and 21—0.5 mg; day 171—0.75 mg; days 394, 401, 409—0.25 mg. One hen received an additional booster of 0.150 mg on day 544.

(c) Antitoxin Collection.

Total yolk immunoglobulin (IgY) was extracted as described in Example 1(c) and the IgY pellet was dissolved in the original yolk volume of PBS thimerosal.

(d) Antigenicity Assessment.

Eggs were collected from day 409 through day 423 to assess whether the toxoid was sufficiently immunogenic to raise antibody. Eggs from the two hens were pooled and antibody was collected as described in the standard PEG protocol (Example 1(c)). Antigenicity of the botulinal toxin was assessed on Western blots. The 150 kD detoxified type A neurotoxin and unmodified, toxic, 300 kD botulinal type A complex (toxin used for intragastric route administration for animal gut neutralization experiments; see Example 6) were separated on a SDS-polyacrylamide reducing gel. The Western blot technique was performed according to the method of Towbin. [H. Towbin et al., Proc. Nat'l Acad. Sci. USA, 76:4350 (1979).] Ten µg samples of botulinum complex and toxoid were dissolved in SDS reducing sample buffer (1% SDS, 0.5% 2-mercaptoethanol, 50 mM Tris, pH 6.8, 10% glycerol, 0.025% w/v bromophenol blue, 10% β-mercaptoethanol), heated at 95° C. for 10 min and separated on a 1 mm thick 5% SDS-polyacrylamide gel. [K. Weber and M. Osborn, *The Proteins*, 3d ed., (H. Neurath and R. L. Hill, eds.), pp. 179–223, Academic Press, N.Y., (1975).] Part of the gel was cut off and the proteins were stained with Coomassie Blue. The proteins in the remainder of the gel were transferred to nitrocellulose using the Milliblot-SDE electro-blotting system (Millipore) according to manufacturer's directions. The nitrocellulose was temporarily stained with 10% Ponceau S [S. B. Carroll and A. Laughon, *DNA Cloning: A Practical Approach*, Vol. III, (D. Glover, ed.), pp. 89–111, IRL Press, Oxford, (1987)] to visualize the lanes, then destained by running a gentle stream of distilled water over the blot for several minutes. The nitrocellulose was immersed in PBS containing 3% BSA overnight at 4° C. to block any remaining protein binding sites.

The blot was cut into strips and each strip was incubated with the appropriate primary antibody. The avian botulinum antibodies (described in (c)) and pre-immune chicken antibody (as control) were diluted 1:125 in PBS containing 1 mg/ml BSA for 2 hours at room temperature. The blots were washed with two changes each of large volumes of PBS, BBS-Tween and PBS, successively (10 min/wash). Goat anti-chicken IgG alkaline phosphatase conjugated secondary antibody (Fisher Biotech) was diluted 1:500 in PBS containing 1 mg/ml BSA and incubated with the blot 2 hours at room temperature. The blots were washed with two changes each of large volumes of PBS and BBS-Tween, followed by one change of PBS and 0.1M Tris-HCl, pH 9.5. Blots were developed in freshly prepared alkaline phosphatase substrate buffer (100 µg/ml NitroBlue Tetrazolium (Sigma), 50 µg/ml 5-bromo-4-chloro-3-indolyl phosphate (Sigma), 5 mM $MgCl_2$ in 50 nM $Na_2CO_3$, pH 9.5).

Figure 1:
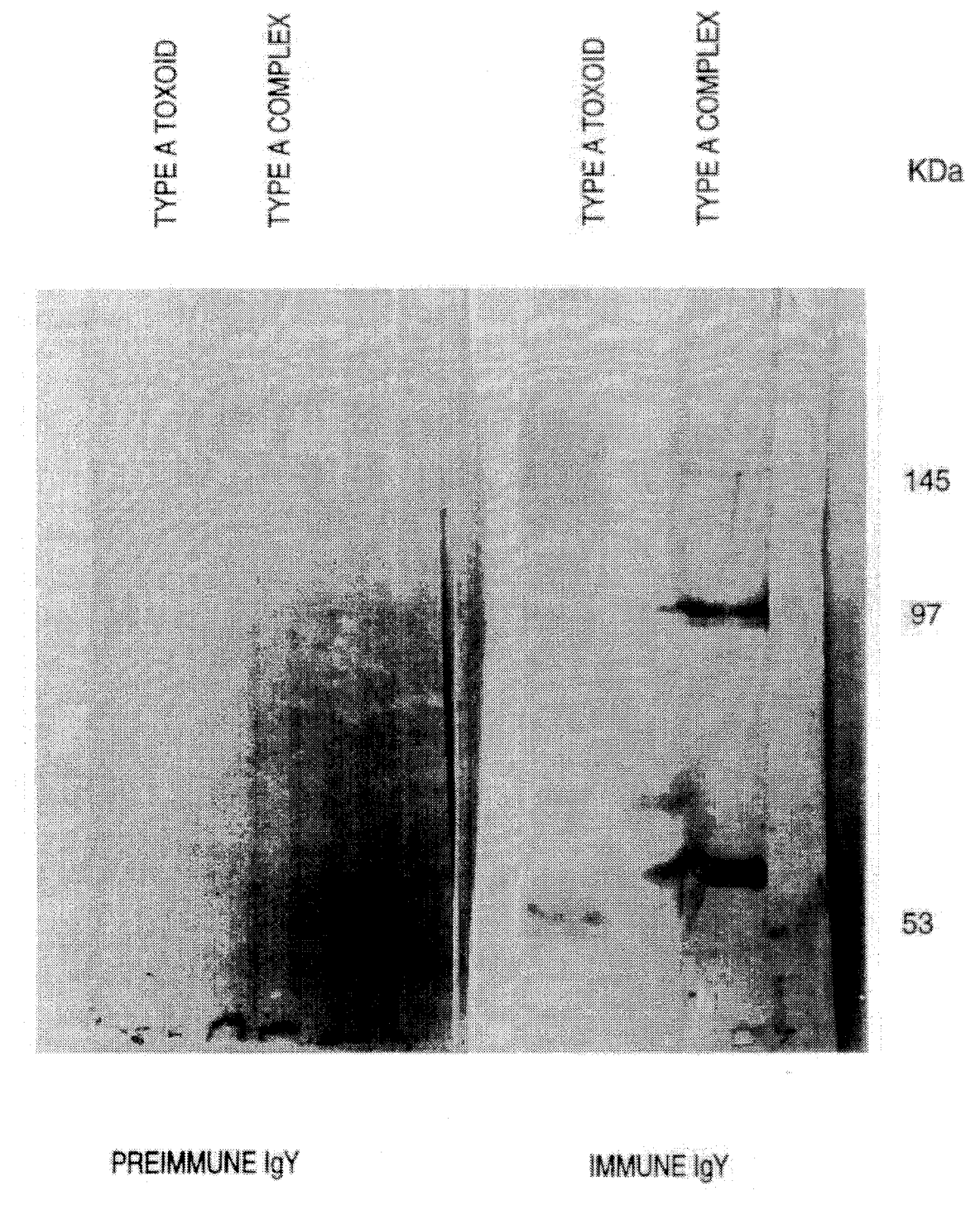

The Western blots are shown in FIG. 1. The antibotulinum IgY reacted to the toxoid to give a broad immunoreactive band at about 145–150 kD on the reducing gel. This toxoid is refractive to disulfide cleavage by reducing agents due to formalin crosslinking. The immune IgY reacted with the active toxin complex, a 97 kD botulinum type A heavy chain and a 53 kD light chain. The preimmune IgY was unreactive to the botulinum complex or toxoid in the Western blot.

(e) Antitoxin Antibody Titer.

The IgY antibody titer to botulinum type A toxoid of eggs harvested between day 409 and 423 was evaluated by ELISA, prepared as follows; Ninety-six-well Falcon Probind plates were coated overnight at 4° C. with 100 µl/well toxoid (B. R. Singh & B. R. Das Gupta, Toxicon 27:403 (1989)) at 2.5 µg/ml in PBS, DH 7.5 containing 0.005% thimerosal. The following day the wells were blocked with PBS containing 1% BSA for 1 hour at 37° C. The IgY from immune or preimmune eggs was diluted in PBS containing 1% BSA and 0.05% Tween 20 and the plates were incubated for 1 hour at 37° C. The plates were washed three times with PBS containing 0.05% Tween 20 and three times with PBS alone. Alkaline phosphatase-conjugated goat-anti-chicken IgG (Fisher Biotech) was diluted 1:750 in PBS containing 1% BSA and 0.05% Tween 20, added to the plates, and incubated 1 hour at 37° C. The plates were washed as before, and p-nitophenyl phosphate (Sigma) at 1 mg/ml in 0.05M $Na_2CO_3$, pH 9.5, 10 mM $MgCl_2$ was added.

The results are shown in FIG. 2. Chickens immunized with the toxoid generated high titers of antibody to the immunogen. Importantly, eggs from both immunized hens had significant anti-immunogen antibody titers as compared to preimmune control eggs. The anti-botulinum IgY possessed significant activity, to a dilution of 1:93,750 or greater.

EXAMPLE 4

Preparation of Avian Egg Yolk Immunoglobulin in an Orally Administrable Form

In order to administer avian IgY antibodies orally to experimental mice, an effective delivery formula for the IgY had to be determined. The concern was that if the crude IgY were dissolved in PBS, the saline in PBS would dehydrate the mice, which might prove harmful over the duration of the study. Therefore, alternative methods of oral administration of IgY were tested. The example involved: (a) isolation of immune IgY; (b) solubilization of IgY in water or PBS, including subsequent dialysis of the IgY-PBS solution with water to eliminate or reduce the salts (salt and phosphate) in the buffer; and (c) comparison of the quantity and activity of recovered IgY by absorbance at 280 nm and PAGE, and enzyme-linked immunoassay (ELISA).

(a) Isolation of Immune IgY.

In order to investigate the most effective delivery formula for IgY, we used IgY which was raised against *Crotalus durissus terrificus* venom. Three eggs were collected from hens immunized with the *C. durissus terrificus* venom and IgY was extracted from the yolks using the modified Polson procedure described by Thalley and Carroll [Bio/Technology, 8:934–938 (1990)] as described in Example 1(c).

The egg yolks were separated from the whites, pooled, and blended with four volumes of PBS. Powdered PEG 8000 was added to a concentration of 3.5%. The mixture was centrifuged at 10,000 rpm for 10 minutes to pellet the precipitated protein, and the supernatant was filtered through cheesecloth to remove the lipid layer. Powdered PEG 8000 was added to the supernatant to bring the final PEG concentration to 12% (assuming a PEG concentration of 3.5% in the supernatant). The 12% PEG/IgY mixture was divided into two equal volumes and centrifuged to pellet the IgY.

(b) Solubilization of the IgY in Water or PBS.

One pellet was resuspended in ½ the original yolk volume of PBS, and the other pellet was resuspended in ½ the original yolk volume of water. The pellets were then centrifuged to remove any particles or insoluble material. The IgY in PBS solution dissolved readily but the fraction resuspended in water remained cloudy.

In order to satisfy anticipated sterility requirements for orally administered antibodies, the antibody solution needs to be filter-sterilized (as an alternative to heat sterilization which would destroy the antibodies). The preparation of IgY resuspended in water was too cloudy to pass through either a 0.2 or 0.45 μm membrane filter, so 10 ml of the PBS resuspended fraction was dialyzed overnight at room temperature against 250 ml of water. The following morning the dialysis chamber was emptied and refilled with 250 ml of fresh $H_2O$ for a second dialysis. Thereafter, the yields of soluble antibody were determined at $OD_{280}$ and are compared in Table 6.

TABLE 6

Dependence of IgY Yield on Solvents

| FRACTION | ABSORBANCE OF 1:10 DILUTION AT 280 nm | PERCENT RECOVERY |
| --- | --- | --- |
| PBS dissolved | 1.149 | 100% |
| $H_2O$ dissolved | 0.706 | 61% |
| PBS dissolved/$H_2O$ dialyzed | 0.885 | 77% |

Resuspending the pellets in PBS followed by dialysis against water recovered more antibody than directly resuspending the pellets in water (77% versus 61%). Equivalent volumes of the IgY preparation in PBS or water were compared by PAGE, and these results were in accordance with the absorbance values (data not shown).

(c) Activity of IgY Prepared with Different Solvents.

An ELISA was performed to compare the binding activity of the IgY extracted by each procedure described above. *C. durissus terrificus* (C.d.t.) venom at 2.5 μg/ml in PBS was used to coat each well of a 96-well microtiter plate. The remaining protein binding sites were blocked with PBS containing 5 mg/ml BSA. Primary antibody dilutions (in PBS containing 1 mg/ml BSA) were added in duplicate. After 2 hours of incubation at room temperature, the unbound primary antibodies were removed by washing the wells with PBS, BBS-tween, and PBS. The species specific secondary antibody (goat anti-Chicken immunoglobulin alkaline-phosphatase conjugate; Sigma Chemical Co.) was diluted 1:750 in PBS containing 1 mg/ml BSA and added to each well of the microtiter plate. After 2 hours of incubation at room temperature, the unbound secondary antibody was removed by washing the plate as before, and freshly prepared alkaline phosphatase substrate (Sigma Chemical Co.) at 1 mg/ml in 50 mM $Na_2CO_3$, 10 mM $MgCl_2$, pH 9.5 was added to each well. The color development was measured on a Dynatech MR 700 microplate reader using a 412 nm filter. The results are shown in Table 7.

TABLE 7

Antigen-Binding Activity of IgY Prepared with Different Solvents

| DILUTION | PRE-IMMUNE | PBS DIS-SOLVED | $H_2O$ DIS-SOLVED | PBS/$H_2O$ |
| --- | --- | --- | --- | --- |
| 1:500 | 0.005 | 1.748 | 1.577 | 1.742 |
| 1:2,500 | 0.004 | 0.644 | 0.349 | 0.606 |
| 1:12,500 | 0.001 | 0.144 | 0.054 | 0.090 |
| 1:62,500 | 0.001 | 0.025 | 0.007 | 0.016 |
| 1:312,500 | 0.010 | 0.000 | 0.000 | 0.002 |

The binding assay results parallel the recovery values in Table 6, with PBS-dissolved IgY showing slightly more activity than the PBS-dissolved/$H_2O$ dialyzed antibody. The water-dissolved antibody had considerably less binding activity than the other preparations.

EXAMPLE 5

Survival of Antibody Activity After Passage Through the Gastrointestinal Tract In order to determine the feasibility of oral administration of antibody, it was of interest to determine whether orally administered IgY survived passage through the gastrointestinal tract. The example involved: (a) oral administration of specific immune antibody mixed with a nutritional formula; and (b) assay of antibody activity extracted from feces.

(a) Oral Administration of Antibody.

The IgY preparations used in this example are the same PBS-dissolved/$H_2O$ dialyzed antivenom materials obtained in Example 4 above, mixed with an equal volume of ENFAMIL (Ross Laboratories). Two mice were used in this experiment, each receiving a different diet as follows:

1) water and food as usual;

2) immune IgY prep dialyzed against water and mixed 1:1 with ENFAMIL. (The mouse was given this mixture as its only source of food and water).

(b) Antibody Activity After Ingestion.

After both mice had ingested their respective fluids, each tube was refilled with approximately 10 ml of the appropriate fluid first thing in the morning. By mid-morning there was about 4 to 5 ml of liquid left in each tube. At this point stool samples were collected from each mouse, weighed, and dissolved in approximately 500 μl PBS per 100 mg stool sample. One hundred and sixty mg of control stools (no antibody) and 99 mg of experimental stools (specific antibody) in 1.5 ml microfuge tubes were dissolved in 800 and 500 μl PBS, respectively. The samples were heated at 37° C. for 10 minutes and vortexed vigorously. The experimental stools were also broken up with a narrow spatula. Each sample was centrifuged for 5 minutes in a microfuge and the supernatants, presumably containing the antibody extracts, were collected. The pellets were saved at 2–8° C. in case future extracts were needed. Because the supernatants were tinted, they were diluted five-fold in PBS containing 1 mg/ml BSA for the initial dilution in the enzyme immunoassay (ELISA). The primary extracts were then diluted five-fold serially from this initial dilution. The volume of primary extract added to each well was 190 μl. The ELISA was performed exactly as described in Example 4.

TABLE 8

| | Specific Antibody Activity After Passage Through the Gastrointestinal Tract | | |
|---|---|---|---|
| DILUTION | PRE-IMMUNE IgY | CONTROL FECAL EXTRACT | EXP. FECAL EXTRACT |
| 1:5 | <0 | 0.000 | 0.032 |
| 1:25 | 0.016 | <0 | 0.016 |
| 1:125 | <0 | <0 | 0.009 |
| 1:625 | <0 | 0.003 | 0.001 |
| 1:3125 | <0 | <0 | 0.000 |

There was some active antibody in the fecal extract from the mouse given the specific antibody in ENFAMIL formula, but it was present at a very low level. Since the samples were assayed at an initial 1:5 dilution, the binding observed could have been higher with less dilute samples. Consequently, the mice were allowed to continue ingesting either regular food and water or the specific IgY in ENFAMIL formula, as appropriate, so the assay could be repeated. Another ELISA plate was coated overnight with 5 μg/ml of C.d.t. venom in PBS.

The following morning the ELISA plate was blocked with 5 mg/ml BSA, and the fecal samples were extracted as before, except that instead of heating the extracts at 37° C., the samples were kept on ice to limit proteolysis. The samples were assayed undiluted initially, and in 5×serial dilutions thereafter. Otherwise the assay was carried out as before.

TABLE 9

| | Specific Antibody Survives Passage Through the Gastrointestinal Tract | | |
|---|---|---|---|
| DILUTION | PRE-IMMUNE IgY | CONTROL EXTRACT | EXP. EXTRACT |
| undiluted | 0.003 | <0 | 0.379 |
| 1:5 | <0 | <0 | 0.071 |
| 1:25 | 0.000 | <0 | 0.027 |
| 1:125 | 0.003 | <0 | 0.017 |
| 1:625 | 0.000 | <0 | 0.008 |
| 1:3125 | 0.002 | <0 | 0.002 |

The experiment confirmed the previous results, with the antibody activity markedly higher. The control fecal extract showed no anti-C.d.t. activity, even undiluted, while the fecal extract from the anti-C.d.t. IgY/ENFAMIL-fed mouse showed considerable anti-C.d.t. activity. This experiment (and the previous experiment) clearly demonstrate that active IgY antibody survives passage through the mouse digestive tract, a finding with favorable implications for the success of IgY antibodies administered orally as a therapeutic or prophylactic.

EXAMPLE 6

In Vivo Neutralization of Type A Botulinum Neurotoxin by Avian Antitoxin Antibody This example demonstrated the ability of PEG-purified antitoxin, collected as described in Example 3, to neutralize the lethal effect of C. botulinum neurotoxin type A in mice. To determine the oral lethal dose ($LD_{100}$) of C. botulinum toxin A, groups of BALB/c mice were given different doses of toxin per unit body weight (average body weight of 24 grams). For oral administration, toxin A complex, which contains the neurotoxin associated with other non-toxin proteins was used. This complex is markedly more toxic than purified neurotoxin when given by the oral route. [I. Ohishi et al., Infect. and Immun., 16:106 (1977).] C. botulinum toxin type A complex, obtained from Eric Johnson (University Of Wisconsin, Madison) was 250 μg/ml in 50 mM sodium citrate, pH 5.5, specific toxicity $3 \times 10^7$ mouse $LD_{50}$/mg with parenteral administration. Approximately 40–50 ng/gm body weight was usually fatal within 48 hours in mice maintained on conventional food and water. When mice were given a diet ad libitum of only Enfamil (Mead Johnson), the concentration needed to produce lethality was approximately 2.5 times higher (125 ng/gm body weight). C. botulinum toxin A concentrations of approximately 200 ng/gm body weight was fatal in mice fed Enfamil containing preimmune IgY (resuspended in Enfamil at the original yolk volume).

The oral $LD_{100}$ of botulinum toxin was also determined in mice that received known amounts of a mixture of preimmune IgY-Ensure (Ross Laboratories) delivered orally through feeding needles. Using a 22 gauge feeding needle, mice were given 250 μl each of a preimmune IgY-Ensure mixture (preimmune IgY dissolved in ¼ original yolk volume) 1 hour before and ½ hour and 5 hours after administering botulinal toxin. Toxin concentrations given orally ranged from approximately 12 to 312 ng/gm body weight (0.3 to 7.5 μg per mouse. *C. botulinum* toxin A complex concentration of approximately 40 ng/gm body weight (1 μg per mouse) was lethal in all mice in less than 36 hours.

Two groups of BALB/c mice, 10 per group, were each given orally a single dose of 1 μg each of botulinal toxin complex in 100 μl of 50 mM sodium citrate pH 5.5. The mice received 250 μl treatments of a mixture of either preimmune or immune IgY in Ensure (¼ original yolk volume) 1 hour before and ½ hour, 4 hours, and 8 hours after botulinal toxin administration. The mice received three treatments per day for two more days. The mice were observed for 96 hours. The survival and mortality are shown in Table 10.

TABLE 10

Neutralization of Botulinal Toxin A In Vivo

| TOXIN DOSE ng/gm | ANTIBODY TYPE | NUMBER OF MICE ALIVE | NUMBER OF MICE DEAD |
|---|---|---|---|
| 41.6 | non-immune | 0 | 10 |
| 41.6 | anti-botulinal toxin | 10 | 0 |

All mice treated with the preimmune IgY-Ensure mixture died within 46 hours post-toxin administration. The average time of death in the mice was 32 hours post toxin administration. Treatments of preimmune IgY-Ensure mixture did not continue beyond 24 hours due to extensive paralysis of the mouth in mice of this group. In contrast, all ten mice treated with the immune anti-botulinal toxin IgY-Ensure mixture survived past 96 hours. Only 4 mice in this group exhibited symptoms of botulism toxicity (two mice about 2 days after and two mice 4 days after toxin administration). These mice eventually died 5 and 6 days later. Six of the mice in this immune group displayed no adverse effects to the toxin and remained alive and healthy long term. Thus, the avian anti-botulinal toxin antibody demonstrated very good protection from the lethal effects of the toxin in the experimental mice.

EXAMPLE 7

Production of an Avian Antitoxin Against *Clostridium Difficile* Toxin A

Toxin A is a potent cytotoxin secreted by pathogenic strains of *C. difficile* that plays a direct role in damaging gastrointestinal tissues. In more severe cases of *C. difficile* intoxication, pseudomembranous colitis can develop which may be fatal. This would be prevented by neutralizing the effects of this toxin in the gastrointestinal tract. As a first step, antibodies were produced against a portion of the toxin. The example involved: (a) conjugation of a synthetic peptide of toxin A to bovine serum albumin; (b) immunization of hens with the peptide-BSA conjugate; and (c) detection of antitoxin peptide antibodies by ELISA.

(a) Conjugation of a Synthetic Peptide of Toxin A to Bovine Serum Albumin.

The synthetic peptide CQTIDGKKYYFNNH$_2$ was prepared commercially (Multiple Peptide Systems, San Diego, Calif.) and validated to be >80% pure by high-pressure liquid chromatography. The eleven amino acids following the cysteine residue represent a consensus sequence of a repeated amino acid sequence found in Toxin A [Wren et al., Infection and Immunity, 59:3151–3155 (1991)]. The cysteine was added to facilitate conjugation to carrier protein.

In order to prepare the carrier for conjugation, BSA (Sigma) was dissolved in 0.01M NaPO$_4$, pH 7.0 to a final concentration of 20 mg/ml and n-maleimidobenzoyl-N-hydroxysuccinimide ester (MBS; Pierce) was dissolved in N,N-dimethyl formamide to a concentration of 5 mg/ml. MBS solution, 0.51 ml, was added to 3.25 ml of the BSA solution and incubated for 30 minutes at room temperature with stirring every 5 minutes. The MBS-activated BSA was then purified by chromatography on a Bio-Gel P-10 column (Bio-Rad; 40 ml bed volume) equilibrated with 50 mM NaPO$_4$, pH 7.0 buffer. Peak fractions were pooled (6.0 ml).

Lyophilized toxin A peptide (20 mg) was added to the activated BSA mixture, stirred until the peptide dissolved and incubated 3 hours at room temperature. Within 20 minutes, the reaction mixture became cloudy and precipitates formed. After 3 hours, the reaction mixture was centrifuged at 10,000×g for 10 min and the supernatant analyzed for protein content. No significant protein could be detected at 280 nm. The conjugate precipitate was washed three times with PBS and stored at 4° C. A second conjugation was performed with 15 mg of activated BSA and 5 mg of peptide and the conjugates pooled and suspended at a peptide concentration of 10 mg/ml in 10 mM NaPO$_4$, pH 7.2.

(b) Immunization of Hens with Peptide Conjugate.

Two hens were each initially immunized on day zero by injection into two subcutaneous and two intramuscular sites with 1 mg of peptide conjugate that was emulsified in CFA (GIBCO). The hens were boosted on day 14 and day 21 with 1 mg of peptide conjugate emulsified in IFA (GIBCO).

(c) Detection of Antitoxin Peptide Antibodies by ELISA.

IgY was purified from two eggs obtained before immunization (pre-immune) and two eggs obtained 31 and 32 days after the initial immunization using PEG fractionation as described in Example 1.

Wells of a 96-well microtiter plate (Falcon Pro-Bind Assay Plate) were coated overnight at 4° C. with 100 μg/ml solution of the toxin A synthetic peptide in PBS, pH 7.2 prepared by dissolving 1 mg of the peptide in 1.0 ml of H$_2$O and dilution of PBS. The pre-immune and immune IgY preparations were diluted in a five-fold series in a buffer containing 1% PEG 8000 and 0.1% tween-20 (v/v) in PBS, pH 7.2. The wells were blocked for 2 hours at room temperature with 150 μl of a solution containing 5% (v/v) Carnation nonfat dry milk and 1% PEG 8000 in PBS, pH 7.2. After incubation for 2 hours at room temperature, the wells were washed, secondary rabbit anti-chicken IgG-alkaline phosphatase (1:750) added, the wells washed again and the color development obtained as described in Example 1. The results are shown in Table 11.

TABLE 11

Reactivity of IgY with Toxin Peptide

| | ABSORBANCE AT 410 nm | |
|---|---|---|
| DILUTION OF PEG PREP | PREIMMUNE | IMMUNE ANTI-PEPTIDE |
| 1:100 | 0.013 | 0.253 |
| 1:500 | 0.004 | 0.039 |
| 1:2500 | 0.004 | 0.005 |

Clearly, the immune antibodies contain titers against this repeated epitope of toxin A.

From the above it should be clear that the present invention provides compositions and methods for effective therapy against clostridial toxin disease therapy. The antitoxins can also be used for diagnostic use.

What is claimed is:

1. A method of treatment of *Clostridium botulinum* neurotoxin disease comprising:
   a) providing:
      i) a therapeutically effective amount of an avian antitoxin composition in an aqueous solution suitable for oral administration wherein said avian antitoxin composition is directed against at least one *Clostridium botulinum* neurotoxin, and
      ii) a subject intoxicated with at least one *Clostridium botulinum* neurotoxin against which said avian antitoxin composition is directed; and
   b) orally administering said avian antitoxin composition to said subject.

2. The method of claim 1 wherein said aqueous solution comprises a nutritional formula.

3. The method of claim 2 wherein said nutritional formula comprises infant formula.

4. A method of prophylactic treatment of *Clostridium botulinum* neurotoxin A disease during a period of treatment for the disease comprising:
   a) providing:
      i) a therapeutically effective amount of an avian antitoxin in an aqueous solution suitable for oral administration wherein said avian antitoxin is directed against *Clostridium botulinum* toxin A, and
      ii) an infant subject; and
   b) orally administering said avian antitoxin to said subject.

5. The method of claim 4 wherein said aqueous solution is a nutritional formula.

6. The method of claim 5 wherein said nutritional formula comprises infant formula.

7. A method of treatment of enteric *Clostridium botulinum* infection comprising:
   a) providing:
      i) a therapeutically effective amount of an avian antitoxin in an aqueous solution suitable for oral administration wherein said avian antitoxin is directed against *Clostridium botulinum* toxin A, and
      ii) an infected subject; and
   b) orally administering said avian antitoxin to said subject.

8. The method of claim 7 wherein said aqueous solution comprises a nutritional formula.

9. The method of claim 8 wherein said nutritional formula comprises infant formula.

10. The method of claim 1 wherein said avian antitoxin composition is directed against at least *Clostridium botulinum* toxin A.

* * * * *